United States Patent [19]

Linsky et al.

[11] Patent Number: 5,007,916

[45] Date of Patent: Apr. 16, 1991

[54] METHOD AND MATERIAL FOR PREVENTION OF SURGICAL ADHESIONS

[75] Inventors: Cary B. Linsky, East Brunswick; Timothy J. Cunningham, Flemington, both of N.J.

[73] Assignee: Johnson & Johnson Medical, Inc., Arlington, Tex.

[21] Appl. No.: 437,234

[22] Filed: Nov. 16, 1989

Related U.S. Application Data

[62] Division of Ser. No. 768,280, Aug. 22, 1985.

[51] Int. Cl.⁵ ............................................. A61B 17/08
[52] U.S. Cl. ..................................... 606/151; 128/156; 8/116.1
[58] Field of Search ........................... 600/37; 606/213; 623/151, 1; 8/116.1; 128/156

[56] References Cited

U.S. PATENT DOCUMENTS

| | | | |
|---|---|---|---|
| 3,054,406 | 9/1962 | Usher | 606/151 |
| 3,328,259 | 6/1967 | Anderson | 128/156 |
| 3,937,223 | 2/1976 | Roth | 606/213 |
| 4,271,070 | 6/1981 | Miyata | 606/151 |
| 4,292,972 | 10/1981 | Pawelchak | 128/156 |
| 4,452,245 | 6/1984 | Usher | 606/151 |
| 4,534,349 | 8/1985 | Barrows | 606/151 |
| 4,626,253 | 12/1986 | Broadmax, Jr. | 128/156 X |

*Primary Examiner*—Alan W. Cannon

[57] ABSTRACT

An absorbable fabric which effectively reduces the incidence of postoperative adhesions when used as a physical barrier at the operative site is a warp knit fabric of oxidized regenerated cellulose or other bioresorbable material. The barrier fabric is particularly characterized by having a density of 8 to 15 mg/cm² and an open area porosity of 12 to 20 percent.

14 Claims, No Drawings

METHOD AND MATERIAL FOR PREVENTION OF SURGICAL ADHESIONS

This is a division of application Ser. No. 768,280, filed Aug. 22, 1985, allowed Oct. 12, 1990.

FIELD OF INVENTION

This invention relates to surgical materials comprising particular fabrics of oxidized cellulose or other bioresorbable material for use in preventing post operative intraperitoneal adhesions.

BACKGROUND OF INVENTION

Post operative intraperitoneal and pelvic adhesions represent a major problem in patients recovering from abdominal surgery. When organs and tissues in the peritoneal cavity are subject to surgical incision or abrasion, there is a tendency for adhesions to form between the affected areas and neighboring tissue.

In the case of intestinal surgery, the incidence of adhesions causing intestinal obstructions has been reported as approximately four times that due to strangulated hernia. The post operative formation or reformation of pelvic adhesions is reported to be a major factor contributing to the relatively poor results obtained in infertility surgery.

Various methods have been suggested for reducing the instance of peritoneal adhesions following surgical intervention, but results have not been entirely favorable. One method involves the application of chemical treating agents to the site of the surgical incision or abrasion in an effort to inhibit the physiological response responsible for the formation of the fibrous tissue which comprises the adhesion mass. In this category are enzymes such as fibrinolysin and papase, polyphloretinphosphate, oxyphenbutazone, a mixture of phenylbutazone and prednisolone, polyvinylpyrrolidone and dextran.

A second approach to preventing the formation of adhesions is to install a physical barrier material between the site of the surgical activity and the neighboring tissue where adhesions are most expected to occur. In this category are silicone sheets such as Silastic*, a medical grade silicone elastomer available from Dow Corning Gelfilm*, an absorbable gelatin film available from Upjohn, and Surgicel*, a knit fabric of oxidized regenerated cellulose available from Johnson & Johnson Products, Inc.

The results obtained with the prior art materials and methods have varied according to different investigators. In the case of oxidized cellulose, for example, very good results were reported by Larssen, Acta Chir Scand 144: pp. 375-378 (1978) and Raftery, Br. J. Surg. Vol. 67 pp. 57-58 (1980); negative results were obtained by Schroder, Acta Chir Scand 148 pp. 595-596 (1982), Yemini, Int. J. Fertil 29 pp. 194-196 (1984) and Soules, Am. J. Obstet & Gyn, Vol. 143 pp. 829-834 (1982); and mixed results were obtained by Nishimura, Jpn. J. Surg. vol. 13 pp. 159-163 (1983).

The present invention concerns an improved, barrier type material for preventing postoperative adhesions which comprises a fabric of oxidized regenerated cellulose (ORC) having a unique construction which is specifically designed for this application. Current fabrics of ORC are primarily intended for use as absorbable hemostatic materials and function well in this capacity. We have discovered that the efficacy of ORC in preventing peritoneal adhesions is affected by fabric construction, and the fabrics intended for use in hemostasis are not optimum for use as an adhesion barrier.

It is accordingly an object of the present invention to provide an improved adhesion barrier material. It is a further object to provide an improved adhesion barrier fabric comprised of oxidized and regenerated cellulose. It is a yet further object of this invention to provide a knit fabric of ORC having a specific construction which is particularly effective as an adhesion barrier. These and other objectives of the present invention will be apparent from the ensuing description and claims.

SUMMARY OF INVENTION

The present invention provides an adhesion barrier comprising a fabric of oxidized regenerated cellulose characterized by having a porosity as defined by open area of 12 to 20 percent and a density of from about 8 to 15 mg/cm$^2$. A typical fabric is prepared from 60 denier, 18 filament bright rayon yarn knitted on a 32 gauge 2 bar warp knitting machine. The knit fabric is oxidized using conventional procedures as described for example in U.S. Pat. No. 3,364,200, the teachings of which are specifically incorporated herein by reference.

ORC fabrics constructed in accordance with the present invention have demonstrated superior performance in reducing the incidence of postoperative adhesion formation when compared to fabrics of ORC heretofore available

DESCRIPTION OF PREFERRED EMBODIMENTS

The improved adhesion barrier fabrics of the present invention are preferably warp knit tricot fabrics characterized by their knit construction and the resulting fabric density and porosity. In the examples which follow, the fabric was produced from continuous filament 60 denier, 18 filament bright rayon yarn on a 32 gauge warp knitting machine. The porosity was determined visually as percent open area using a light microscope in conjunction with an image analyzer.

The efficacy of various barrier fabrics of the present invention as compared to commercially available Surgicel* ORC absorbable hemostatic material was determined by the uterine horn model using female New Zealand white rabbits weighing 2.0 to 3.5 kg. After acclimating for two weeks, the animals were fasted overnight prior to surgery. Using sterile surgical techniques, the animals were anesthetized and a laparotomy performed through a lower midline incision. The uterine horns were identified and the serosal surfaces of each horn abraded with a scalpel 1 cm. from the bifurcation for a distance of 5 cm. The tissues were abraded until punctate hemorrhage and engorgement of the blood vessels occurred.

A piece of barrier fabric 3.5×7.6 cm was placed around each uterine horn to completely cover the area of serosal abrasion, and then moistened with sterile saline. In control animals, the areas of abrasion were washed with saline but otherwise left untreated. The incision was closed and animals allowed to recover postoperatively.

After 14 days, the animals were sacrificed and examined for adhesions in contact with the scraped uterine horn. The extent of adhesion was graded on the following numerical scale.

0 - No adhesion 1.0 - Adhesions over 25% of area 2.0 - Adhesions over 50% of area
3.0 - Adhesions over entire area The severity of the adhesions were graded on the following numerical scale:
 0 - Easily separable
 0.5 - Resistant to separation
 1.0 - Dissection required A composite score computed as the sum of the individual scores for extent and severity of adhesion was recorded for each uterine horn, the score having a possible numerical range of from 0 to 4.

The adhesion results obtained in the animal studies with four test fabrics having the indicated physical properties and two controls were as follows:

|  | Test Fabric | | | | Controls | |
|---|---|---|---|---|---|---|
|  | T-1 | T-2 | T-3 | T-4 | A | B |
| Physical Properties |  |  |  |  |  |  |
| density (d), mg/cm$^2$ | 11.6 | 8.1 | 11.5 | 10.6 | 6.8 | N/A |
| porosity (p), % | 16.5 | 19.5 | 18.9 | 17.1 | 35.0 | N/A |
| p/d ratio | 1.4 | 2.4 | 1.6 | 1.6 | 5.1 | N/A |
| Animal Studies |  |  |  |  |  |  |
| No. of Animals | 3 | 3 | 3 | 4 | 6 | 6 |
| Adhesion Scores | 2.5 | 1.0 | 1.5 | 1.5 | 3.0 | 2.0 |
|  | 3.0 | 0 | 0 | 1.0 | 3.0 | 3.5 |
|  | 0 | 0 | 1.0 | 0.25 | 4.0 | 1.0 |
|  | 0 | 1 | 0.5 | 0.5 | 4.0 | 2.0 |
|  | 0 | 0 | 1.5 | 0.25 | 4.0 | 0 |
|  | 0 | 0.5 | 0.5 | 0 | 4.0 | 2.0 |
|  |  |  |  |  | 0.5 | 3.0 | 3.5 |
|  |  |  |  |  | 0.5 | 3.0 | 3.5 |
|  |  |  |  |  | 2.0 | 4.0 |
|  |  |  |  |  | 1.5 | 4.0 |
|  |  |  |  |  | 2.5 | 4.0 |
|  |  |  |  |  | 3.0 | 4.0 |
| Avg. Adh. Score | 0.9 | 0.4 | 0.8 | 0.6 | 3.2 | 2.8 |

Control A employed Surgicel* absorbable hemostatic material, a knit fabric produced from 150 denier, 90 filament bright rayon yarn on a circular knitting machine. Control B refers to the animals having no applied barrier fabric.

As indicated by the above adhesion score data there was no significant difference between Control A using Surgicel* fabric and Control B using no physical barrier. This confirms the results reported in the literature by most investigators. The test fabrics of the present invention, however, show a clear and significant advantage over Controls A and B. While the test fabrics generally had one or two individual scores of 1.5 or higher, such variability is normal in a test of this kind where physiological factors may vary from animal to animal, and only the average adhesion score based on at least six individual scores is significant. In the case of the test materials, all had an average adhesion score of less than 1.0, indicating a significant reduction in both the area and severity of adhesions occurring with the use of this material.

The porosity of the fabric as indicated by the amount of open area and the fabric density appear to be critical parameters in defining ORC knit fabrics which perform effectively to prevent or reduce post operative adhesions. The relationship between density (d) and porosity (p) as indicated by the numerical ratio of p/d also appears to be a factor. Three additional fabrics prepared by tricot knitting the same yarn as above to a higher or lower porosity and/or density than specified for the fabrics of the present invention produced significantly higher adhesion scores, as shown by the following data.

|  | TC-1 | TC-2 | TC-8 |
|---|---|---|---|
| density, mg/cm$^2$ | 17.9 | 14.6 | 8.7 |
| porosity, % | 9.6 | 13.2 | 25.6 |
| p/d ratio | 0.5 | 0.9 | 2.9 |
| Avg. Adhesion Score | 1.8 | 2.1 | 2.5 |

While not wishing to be bound by theory, an ORC fabric is believed to affect adhesion formation by a process wherein the transformation of the ORC fabric into a gelatinous mass effectively coats and protects the injured area. It has been noted in the literature, however, (Nishimura, supra) that ORC provides an effective nidus for clot formation, and that where post and intraoperative ooze produce fibrin clots in the ORC, dense adhesions were found. Thus, a specific function of the ORC fabric construction may be to reduce the formation of fibrin clots, or provide a gelatinous coating which is less subject to the attachment of fibrin bands, and thereby obtain a consequent reduction in adhesion formation.

Regardless of the exact mechanism by which the fabrics of the present invention obtain their superior performance in reducing postoperative adhesions, the effective values for the density and porosity of the ORC fabrics are believed to be in the following ranges:
 density, 8.0–15 mg/cm$^2$, preferably 9.0–13 mg/cm$^2$
 porosity, 12–20% open area, and preferably 15–19%
 numerical ratio of porosity to density, 1.0 or greater.

The fabrics of the present invention are preferably warp knit not only to obtain the effective values of density and porosity, but also to provide good handling properties as desired for adhesion barriers. While warp knit fabrics clearly provide the desired combination of properties for an effective adhesion barrier, equivalent fabrics of other constructions such as nonwoven materials may be used and are within the scope of the present invention. The critical handling property is one of softness and conformability which allows a fabric of the proper density and porosity to conform to the surface of the injured tissue. Thus, in the case of the warp knit ORC fabric of the present invention, the gelatinous mass formed during the resorption process is believed to form an intimate coating over the injured surface to more effectively prevent the formation of adhesions.

While the fabrics used in the examples herein were all derived from 60 denier, 18 filament continuous filament bright rayon yarn, this is merely a convenient yarn for warp knitting and the present invention is not limited thereby. As will be apparent to those skilled in the art, substantially equivalent fabrics which would be expected to produce substantially equivalent results in adhesion prevention could be produced from at least 40 to 80 denier yarns having 10 to 25 individual filaments.

The barrier fabrics of the present invention may furthermore be constructed of other bioresorbable materials which have the same physical characteristics and provide the same biological effect as oxidized regenerated cellulose, as for example, proteinaceous fibers such as those derived from algin or collagen. Other variations in fabric construction or composition which do not depart from the scope of the present invention will also be apparent to those skilled in the art.

We claim:

1. A postoperative adhesion barrier comprising a conformable fabric constructed of a bioresorbable material, said fabric being characterized by having a density of 8.0 to 15 mg/cm$^2$ and a porosity of 12 to 20 percent open area.

2. The adhesion barrier of claim 1 wherein said material is selected from the group consisting of oxidized regenerated cellulose and proteinaceous fibers.

3. The adhesion barrier of claim 1 wherein the numerical ratio of said porosity, in percent open area, to said density, in mg/cm$^2$, is 1.0 or greater.

4. The adhesion barrier of claim 1 wherein said fabric has a knit or nonwoven construction.

5. The adhesion barrier of claim 1 wherein said fabric has a warp knit construction.

6. An absorbable, postoperative adhesion barrier comprising a warp knit fabric of oxidized regenerated cellulose, said fabric being characterized by having a density of 8.0 to 15 mg/cm$^2$ and a porosity of 12 to 20% open area.

7. The adhesion barrier of claim 6 wherein said fabric is derived from continuous filament bright rayon yarn having a total denier of from about 40 to 80 and containing from 10 to 25 individual filaments.

8. The adhesion barrier of claim 6 wherein said fabric is derived from a 60 denier, 18 filament bright rayon yarn.

9. The adhesion barrier of claim 6 wherein said fabric is a tricot knit fabric.

10. The adhesion barrier of claim 6 wherein the numerical ratio of said porosity, in percent open area, to said density, in mg/cm$^2$, is 1.0 or greater.

11. An absorbable, postoperative adhesion barrier comprising a warp knit tricot fabric of oxidized regenerated cellulose, said fabric being characterized by a density of 9 to 13 mg/cm$^2$ and an open area porosity of 15 to 19 percent.

12. The adhesion barrier of claim 11 wherein said fabric is derived from continuous filament bright rayon yarn having a total denier of from about 40 to 80 and containing from 10 to 25 individual filaments.

13. The adhesion barrier of claim 11 wherein said fabric is derived from a 60 denier, 18 filament bright rayon yarn.

14. The adhesion barrier of claim 11 wherein the numerical ratio of porosity to density is 1.0 or greater.

* * * * *